US006982256B2

(12) United States Patent
Votteler et al.

(10) Patent No.: US 6,982,256 B2
(45) Date of Patent: Jan. 3, 2006

(54) TOLERANCE OF 4-(4-(2-PYRROLYLCARBONYL)-1-PIPERAZINYL)-3-TRIFLUOROMETHYL-BENZOYLGUANIDINE IN INTRAVENOUS ADMINISTRATION

(75) Inventors: Christine Votteler, Maselheim-Sulmingen (DE); Bernd Kruss, Hochdorf (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/237,918

(22) Filed: Sep. 9, 2002

(65) Prior Publication Data

US 2003/0069207 A1 Apr. 10, 2003

Related U.S. Application Data

(60) Provisional application No. 60/323,477, filed on Sep. 19, 2001.

(30) Foreign Application Priority Data

Sep. 7, 2001  (DE) ......................................... 101 44 030

(51) Int. Cl.
 A61K 31/724  (2006.01)

(52) U.S. Cl. ............... 514/58; 514/253.13; 514/254.01; 514/255.01; 514/400.12; 514/21; 514/374; 536/103; 536/46; 544/360; 544/372; 544/379; 548/235; 435/320.1; 424/439; 424/85.1

(58) Field of Classification Search .................. 514/58, 514/253.13, 254.01, 255.01, 400, 12, 21, 514/374; 536/103, 46; 544/360, 372, 379; 548/235; 435/320.1; 424/439, 85.1
See application file for complete search history.

(56) References Cited

U.S. PATENT DOCUMENTS

| 4,727,064 | A |   | 2/1988  | Pitha |
| 5,324,750 | A | * | 6/1994  | Lincoln et al. ............. 514/570 |
| 6,323,207 | B1 | * | 11/2001 | Eickmeier et al. ..... 514/253.13 |
| 6,407,079 | B1 |   | 6/2002  | Muller et al. |

FOREIGN PATENT DOCUMENTS

| DE | 198 43 489 A1 | 3/2000 |
| EP | 0 149 197 B2  | 1/1997 |
| EP | 1 029 872 A1  | 8/2000 |
| WO | WO 96 19970   | 7/1996 |
| WO | WO 99 10008   | 3/1999 |
| WO | WO 00/04888 A2 | 2/2000 |
| WO | WO 00 17176   | 3/2000 |
| WO | WO 02/064563 A1 | 8/2002 |

OTHER PUBLICATIONS

Loftsson, T. et al; "Pharmaceutical Applications of Cyclodextrins. 1. Drug Solubilization and Stabilization"; J. Pharm. Sci. 1996, 85, pp. 1017–1025.

Jäervinen, T. et al; "Sulfobutyl Ether beta–Cyclodextrin (SBE–beta–CD) in Eyedrops Improves the Tolerability of a Topically Applied Pilocarpine Prodrug in Rabbits"; J Ocul. Pharmacol. Ther., 1995, 11, pp. 95–106.

Arima, et al; "Enhanced Rectal Absorption and Reduced Local Irritation of the Anti–inflammatory Drug Ethyl 4–Biphenylylacetate in Rats by Complexation with Water-–Soluble beta–Cyclodextrin Derivatives and Formulations as Oleaginous Suppository"; J. Pharm. Sci, 1992, 81, pp. 1119–1125.

Pitha, J. et al; "Hydroxypropyl–beta–cyclodextrin: preparation and characterization; effects on solubility of drugs"; Int J Pharmaceutics, 1986, 29, pp. 73–82.

Dass, C. R. et al; "Apolipoprotein A–1, Phospholipid Vesicles, and Cyclodextrins as Potential Anti–Atherosclerotic Drugs: Delivery, Pharmacokinetics, and Efficacy"; Drug Delivery, 2000, 7, pp. 161–182.

Gumina, R. J. et al; "Inhibition of the Na+/H+ Exchanger Confers Greater Cardioprotection Against 90 Minutes of Myocardial Ischemia Than Ischemic Preconditioning in Dogs", Circulation, 1999, 100, pp. 2519–2526.

Nambu, N. et al; "Influence of Inclusion of Nonsteroidal Antiinflammatory Drugs with beta–Cyclodextrin on the Irritation to Stomach of Rats upon Oral Administration"; Chem. Pharm. Bull. 1978, 26, pp. 3609–3612.

Eickmeier, C. et al, "Benzoylguanidine Salt and Hydrates Thereof"; U.S. Appl. No. 10/057,597, filed Jan. 25, 2002.

Loftsson, T. et. al.; "Effects of 2–hydroxypropyl–Beta–cyclodexinin on the aqueous solubility of drugs and transdermal delivery of 17Beta–estradiol"; Acta Pharm. Nord. 1 (4) 1989; pp. 185–194.

Rajewski, R., et. al.; "Pharmaceutical Applications of Cyclodextrins. 2. In Vivo Drug Delivery". Journal of Pharmaceutical Sciences, vol. 85; No. 11, Nov., 1996, pp. 1142–1169.

\* cited by examiner

Primary Examiner—James O. Wilson
Assistant Examiner—Devesh Khare
(74) Attorney, Agent, or Firm—Michael P. Morris; Philip I. Datlow; Mary-Ellen Devlin

(57) ABSTRACT

The invention relates to new formulations for improving the local tolerance of intravenously administered 4-(4-(2-pyrrolylcarbonyl)-1-piperazinyl)-3-trifluoromethyl-benzoylguanidine or one of the pharmacologically acceptable acid addition salts thereof.

16 Claims, No Drawings

TOLERANCE OF 4-(4-(2-PYRROLYLCARBONYL)-1-PIPERAZINYL)-3-TRIFLUOROMETHYL-BENZOYLGUANIDINE IN INTRAVENOUS ADMINISTRATION

RELATED APPLICATIONS

Benefit of U.S. Provisional Application Ser. No. 60/323,477, filed on Sep. 19, 2001 is hereby claimed, and said provisional application is herein incorporated by reference in its entirety.

FIELD OF THE INVENTION

The invention relates to formulations of 4-(4-(2-pyrrolylcarbonyl)1-piperazinyl)-3-trifluoromethyl-benzoylguanidine, or one of the pharmacologically acceptable acid addition salts thereof, as the active ingredient which improve the local tolerance, i.e. the tolerance at the injection or infusion site, of the active ingredient when administered intravenously. The formulations according to the invention include the mixing and complexing of the active ingredient with cyclodextrins, particularly with hydroxypropyl-β-cyclodextrin (HPβCD), the mixing and complexing of the active ingredient with cyclodextrins and hydroxy acids, the enveloping of the active ingredient in polymer coils, e.g. in poloxamer, polyvinylpyrrolidone or polysorbate, as well as the incorporation of the active ingredient in mixed micelles comprising a phospholipid and a bile salt.

BACKGROUND OF THE INVENTION

Compounds of general formula (I):

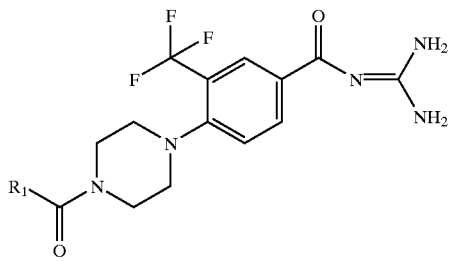

(I)

wherein

R$_1$ may denote C$_1$–C$_8$-alkyl, heteroaryl which is unsubstituted or mono- or polysubstituted with a branched or unbranched C$_1$–C$_4$-alkyl group, a cycloalkyl group, a branched or unbranched C$_1$–C$_4$-alkoxy group, an NH$_2$-group or a primary or secondary amino group, a trifluoromethyl group, a cyano or nitro group or halogen, aryl which is unsubstituted or mono- or polysubstituted with a branched or unbranched C$_1$–C$_4$-alkyl group, a branched or unbranched C$_1$–C$_4$-alkoxy group, a NH$_2$-group or a primary or secondary amino group of a trifluoromethyl group, a hydroxy, cyano or nitro group or halogen or with a 5- or 6-membered heteroaryl group which may contain one, two, three, four or five heteroatoms selected from among nitrogen, oxygen or sulphur, which may be identical or different, alkylaryl which is unsubstituted or mono- or polysubstituted in the aryl and/or alkyl partial structure with a branched or unbranched C$_1$–C$_4$-alkyl group, a branched or unbranched C$_1$–C$_4$-alkoxy group, an NH$_2$-group or a primary or secondary amino group of a trifluoromethyl group of a cyano or nitro group or halogen, optionally in the form of the individual tautomers or possibly enantiomers and the mixtures thereof as well as in the form of the free bases or the corresponding acid addition salts with pharmacologically acceptable acids, are known from published German Application DE 198 43 489. This publication also describes, in particular, the compound 4-(4-(2-pyrrolylcarbonyl)-1-piperazinyl)-3-trifluoromethyl-benzoylguanidine methanesulphonate, namely

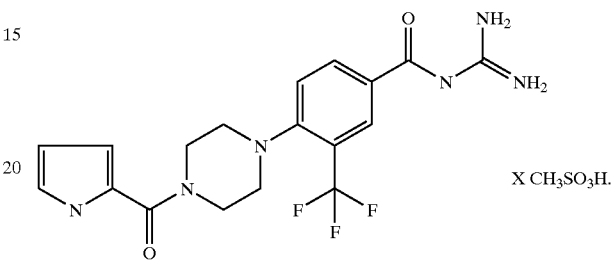

X CH$_3$SO$_3$H.

Because of their activity as inhibitors of the cellular Na$^+$/H$^+$ exchange, compounds of this kind may be used as active substances in pharmaceutical compositions or as intermediate products for preparing such active substances. The compounds according to the invention are effective against arrhythmias such as those which occur in cases of hypoxia, for example. They may also be used to treat diseases related to ischaemia (such as cardiac, cerebral, gastrointestinal diseases—such as mesenteric thrombosis/embolism, pulmonary, renal ischaemia, ischaemia of the liver, ischaemia of the skeletal musculature). Such diseases may be, for example, coronary heart disease, myocardial infarction, angina pectoris, stable angina pectoris, ventricular arrhythmias, subventricular arrhythmias, cardiac insufficiency—and also to assist bypass operations, to assist open heart surgery, to assist operations which require interruption of the blood supply to the heart and to assist heart transplants—embolism in the pulmonary circulation, acute or chronic kidney failure, chronic kidney insufficiency, cerebral infarction, reperfusion injury caused by the restoration of circulation to areas of the brain after the removal of vascular occlusions and acute and chronic circulatory disorders of the brain. The abovementioned compounds may also be used in conjunction with thrombolytic agents such as t-PA, streptokinase and urokinase.

When the ischaemic heart is reperfused (e.g. after an attack of angina pectoris or a myocardial infarction) there may be irreversible damage to cardiomyocytes in the affected region. The compounds according to the invention have a cardioprotective effect, inter alia, in such a case.

The field of ischaemia should also include the prevention of damage to transplants (e.g. as a protection for the transplanted organ—such as for example a liver, kidney, heart or lung—before, during and after implantation as well as during storage of the transplants), which may occur in connection with transplants. The compounds are, moreover, drugs with a protective effect during angioplastic surgical procedures on the heart and on peripheral blood vessels.

In essential hypertension and diabetic nephropathy the cellular sodium proton exchange is increased. The compounds according to the invention are therefore suitable as inhibitors of this exchange for the preventive treatment of these diseases.

The compounds according to the invention are further characterised by a strongly inhibiting effect on the proliferation of cells. Therefore, the compounds are useful as drugs for treating illnesses in which cell proliferation plays a primary or secondary role and may be used as agents against cancers, benign tumours, or for example prostatic hypertrophy, atherosclerosis, organ hypertrophies and hyperplasias, fibrotic diseases and late complications of diabetes.

Moreover, compounds of this type are known to be capable of favourably influencing the blood levels of the serum lipoproteins.

When they are administered parenterally some local intolerances occasionally arise. 4-(4-(2-Pyrrolylcarbonyl)-1-piperazinyl)-3-trifluoromethyl-benzoylguanidine hydrochloride was found to have a haemolytic activity and to be locally poorly tolerated after intravenous administration.

The poor tolerance often has completely different causes. On the one hand it could be the physical/chemical properties of the preparation such as its pH value, buffer capacity, tonicity, which deviate to a greater or lesser extent from the physiological conditions at the injection or infusion site and lead to unwanted reactions there, particularly when administered over lengthy periods. On the other hand the active substance itself may interact undesirably with the morphological structures at the injection or infusion site.

The following procedures for improving tolerance are known from Way, S. and Brazeau, G.: "Techniques to Reduce Pain and Irritation", Interpharm Press 1999, p. 215 ff, p. 247 ff:

a) diluting the medication with a conventional carrier, equivalent to administering it over a longer period
b) administering it through large blood vessels, i.e. a central vein instead of a peripheral vein
c) giving a local anaesthetic or analgesic beforehand or simultaneously.

The principle of these procedures is to reduce the actual concentration of the formulation or of the active substance.

The disadvantages of these measures, depending on the indication, are that a) as a result of the dilution an undesirably large volume is administered, resulting in an undesirably high fluid loading of the patient;
b) the period of administration is extended;
c) administration through a central vein requires experience and technical equipment which is not always available in emergencies;
d) the use of a local anaesthetic might possibly be contraindicated.

The objective of the present invention is to formulate the sodium-proton exchange inhibitor 4-(4-(2-pyrrolylcarbonyl)-1-piperazinyl)-3-trifluoromethyl-benzoylguanidine or one of the pharmacologically acceptable acid addition salts thereof in such a way that, immediately during and after intravenous administration, there is no local intolerance of the kind observed when aqueous, isotonic solutions were administered to animals without any measures being taken to improve tolerance. The improvement in tolerance should not be achieved by any of the conventional methods such as increasing the volume administered or extending the infusion period. The improvement in local tolerance is of crucial importance for emergency injections of a bolus.

DETAILED DESCRIPTION OF THE INVENTION 4-(4-(2-pyrrolylcarbonyl)-1-piperazinyl)-3-trifluoromethyl-benzoylguanidine is a sodium proton exchange inhibitor with two main indications:

1. acute myocardial infarction combined with reperfusion therapy
2. patients in whom a coronary artery bypass operation has to be carried out with a high risk of perioperative myocardial necrosis.

In the following description the term "active substance", on its own or in combination, always denotes 4-(4-(2-pyrrolylcarbonyl)-1-piperazinyl)-3-trifluoromethyl-benzoylguanidine hydrochloride, unless otherwise stated. Both a monohydrate and a hemihydrate of 4-(4-(2-pyrrolylcarbonyl)-1-piperazinyl)-3-trifluoromethyl-benzoylguanidine hydrochloride may be obtained. For all the experiments the hemihydrate was used. The quantitative data used hereinafter always relate to the free base; i.e. the quantities specified correspond to the theoretical amount of free base, whereas in reality a correspondingly larger amount of hemihydrate was added. In each case glucose was used to render the solution isotonic. The isotonic nature of the solutions was checked in each case by lowering the freezing point. In in-vitro haemolysis tests in each case the solution to be tested was mixed with citrated human blood in the ratio 1:1 and kept at 37° C. during the incubation period.

For both types of indications an intravenous form for a one-time administration is required, in the former case a bolus injection, as this is an emergency indication, and in the latter case a solution for infusion during a coronary artery bypass operation. The intravenous preparation contains the active substance in doses of 150 mg/person—600 mg/person. The volumes to be administered are in the range from 15 ml–250 ml. The active substance concentrations are thus between 0.6 mg/ml and 40 mg/ml.

The haemolytic activity and local intolerance of aqueous, isotonic active substance solutions without any measures to improve tolerance increases with the concentration of the active substance. In an in vitro haemolysis test with an incubation period of two hours the following findings are observed:

| active substance concentration (mg/ml) | degree of haemolysis (%) |
| --- | --- |
| 0.5 | 0 |
| 1.0 | 1 |
| 1.5 | 4 |

In an in vitro haemolysis test with an incubation period of 45 minutes the following findings are observed:

| active substance concentration (mg/ml) | degree of haemolysis (%) |
| --- | --- |
| 1.5 | 0 |
| 10.0 | 100 |

Even a concentration of 0.75 mg/ml proved to be poorly tolerated in a trial on rats (30 minutes' infusion into the caudal vein).

An improvement in tolerance according to the invention can be achieved by the addition of a cyclodextrin, particularly a pharmacologically acceptable substituted β-cyclodextrin such as HPβCD, to form a mixture or complex thereof with the 4-(4-(2-pyrrolylcarbonyl)-1-piperazinyl)-3-trifluoromethyl-benzoylguanidine, or one of the pharmacologically acceptable acid addition salts thereof.

In an in vitro haemolysis test with an incubation period of 45 minutes no haemolysis is observed on 1% aqueous isotonic active substance solutions containing 10% HPβCD:

| active substance (mg/ml) | HPβCD (mg/ml) | degree of haemolysis (%) |
|---|---|---|
| 10 | 0 | 100 |
| 10 | 100 | 0 |

These solutions proved to be locally well-tolerated in a study on rabbits (bolus and 8 minutes infusion).

In the second step the appropriate ratio of HPβCD to active substance was determined from the local tolerance in dogs. A weight ratio of 10:1 (HPβCD to active substance) proved to be suitable both in the form of a bolus (active substance concentration 10 mg/ml) and also in an infusion (active substance concentration between 1.5 mg/ml and 3 mg/ml). This corresponds to a molar ratio of about 3:1 Further tests showed that even a ratio of HPβCD to active substance of 6.67:1 is not haemolytic at an active substance concentration of 9 mg/ml.

Another embodiment of the invention relates to improving the degree of tolerance by mixing and complexing 4-(4-(2-pyrrolylcarbonyl)-1-piperazinyl)-3-trifluoromethyl-benzoylguanidine, or one of the pharmacologically acceptable acid addition salts thereof, with a cyclodextrin, particularly a pharmacologically acceptable substituted β-cyclodextrin such as HPβCD, and a hydroxy acid.

The amount of cyclodextrin required to improve the tolerance of 4-(4-(2-pyrrolylcarbonyl)-1-piperazinyl)-3-trifluoromethyl-benzoylguanidine can be reduced by the formation of a ternary complex consisting of 4-(4-(2-pyrrolylcarbonyl)-1-piperazinyl)-3-trifluoromethyl-benzoylguanidine, the appropriate cyclodextrin and hydroxy acid. Hydroxy acids which may be used include for example malic acid, acetic acid, lactic acid, tartaric acid and citric acid. Preferably, citric acid is used.

A further object of the invention is the improvement of tolerance by enveloping 4-(4-(2-pyrrolylcarbonyl)-1-piperazinyl)-3-trifluoromethyl-benzoylguanidine, or one of the pharmacologically acceptable acid addition salts thereof, in polymer coils, e.g. in a poloxamer, polyvinylpyrrolidone or polysorbate.

The enveloping of 4-(4-(2-pyrrolylcarbonyl)-1-piperazinyl)-3-trifluoromethyl-benzoyl-guanidine, or one of the pharmacologically acceptable acid addition salts thereof, in a polymer, e.g. Poloxamer 188, leads to a reduction in the haemolytic activity and the poor tolerance of 4-(4-(2-pyrrolylcarbonyl)-1-piperazinyl)-3-trifluoromethyl-benzoylguanidine. In an in vitro haemolysis test with an incubation period of 45 minutes the following findings are observed on 1% aqueous isotonic active substance solutions containing different amounts of Poloxamer 188:

| active substance (mg/ml) | Poloxamer 188 (mg/ml) | degree of haemolysis (%) |
|---|---|---|
| 10 | 0 | 99 |
| 10 | 100 | 4 |
| 10 | 200 | 0 |

An aqueous isotonic solution containing 1.5 mg/ml of 4-(4-(2-pyrrolylcarbonyl)-1-piperazinyl)-3-trifluoromethyl-benzoylguanidine and 100 mg/ml of Poloxamer 188 proved to be better tolerated in a study on rats (30 minutes infusion into the caudal vein) than an aqueous isotonic solution containing 1.5 mg/ml of 4-(4-(2-pyrrolylcarbonyl)-1-piperazinyl)-3-trifluoromethyl-benzoylguanidine without a tolerance-enhancing excipient.

Another example of a tolerance-enhancing polymer is polyvinylpyrrolidone 17 PF (PVP 17 PF). In an in vitro haemolysis test with an incubation period of 45 minutes a degree of haemolysis of only 17% is observed on an aqueous isotonic solution containing 10 mg/ml of 4-(4-(2-pyrrolylcarbonyl)-1-piperazinyl)-3-trifluoromethyl-benzoylguanidine and 100 mg/ml of PVP 17 PF.

Yet another embodiment of the invention relates to the improvement in tolerance achieved by incorporating 4-(4-(2-pyrrolylcarbonyl)-1-piperazinyl)-3-trifluoromethyl-benzoylguanidine, or one of the pharmacologically acceptable acid addition salts thereof, in mixed micelles comprising a phospholipid and a bile salt.

One phospholipid might be, for example, a soya lecithin with a high proportion of phosphatidylcholine. Examples of suitable bile salts are the sodium salts of cholic acid and glycocholic acid. In in vitro haemolysis tests with an incubation period of 45 minutes the following findings are observed on 1% aqueous isotonic active substance solutions containing different amounts of phospholipid and sodium cholate:

| active substance (mg/ml) | phospholipid (mg/ml) | sodium cholate (mg/ml) | degree of haemolysis (%) |
|---|---|---|---|
| 10 | 150 | 100 | 0 |
| 10 | 75 | 50 | 7 |

These solutions proved to be locally well-tolerated in a study of rabbits (bolus and 8 minutes infusion).

If sodium cholate is replaced by sodium glycocholate, the following findings are observed on the following aqueous isotonic solutions in in vitro haemolysis tests:

| active substance (mg/ml) | phospholipid (mg/ml) | sodium glycocholate (mg/ml) | degree of haemolysis (%) |
|---|---|---|---|
| 10 | 60 | 36 | 7 |
| 10 | 60 | 32 | 2 |

The following Examples are intended to illustrate the invention without restricting it.

EXAMPLES OF FORMULATIONS

As the active substance is prone to hydrolysis, only anhydrous formulations are stable. Therefore, lyophilisates have been developed, which have to be reconstituted before use.

Composition of the Lyophilisate

| name of ingredient | mg per injection vial | function |
|---|---|---|
| 4-(4-(2-pyrrolylcarbonyl)-1-piperazinyl)-3-trifluoromethyl-benzoyl-guanidine hydrochloride (calculated as free base) | 150 | active substance |
| HPβCD | 1500 | improvement in local tolerance of the active substance |

Reconstitution solution for a volume to be administered of 50 ml (infusion):

5% aqueous glucose solution

Reconstitution solution for a volume to be administered of 15 ml (bolus):

3.3% aqueous glucose solution

Composition of the Lyophilisate

| name of ingredient | mg per injection vial | function |
|---|---|---|
| 4-(4-(2-pyrrolylcarbonyl)-1-piperazinyl)-3-trifluoromethyl-benzoyl-guanidine hydrochloride (calculated as free base) | 150 | active substance |
| soya lecithin | 2250 | improvement in local tolerance of the active substance |
| sodium cholate | 1500 | |

Reconstitution solution for a volume to be administered of 50 ml (infusion):

4% aqueous glucose solution

Reconstitution solution for a volume to be administered of 15 ml (bolus):

2% aqueous glucose solution

Composition of the Lyophilisate

| name of ingredient | mg per injection vial | function |
|---|---|---|
| 4-(4-(2-pyrrolylcarbonyl)-1-piperazinyl)-3-trifluoromethyl-benzoyl-guanidine hydrochloride (calculated as free base) | 150 | active substance |
| soya lecithin | 900 | improvement in local tolerance of the active substance |
| sodium glycocholate | 540 | |

Reconstitution solution for a volume to be administered of 15 ml (bolus):

3.3% aqueous glucose solution

We claim:

1. A pharmaceutical composition comprising a mixture or a complex, or both, of 4-(4-(2-pyrrolylcarbonyl)-1-piperazinyl)-3-trifluoromethyl-beazoylguanidine, or one of the pharmacologically acceptable acid addition salts thereof, and a pharmacologically acceptable cyclodextrin.

2. A pharmaceutical composition according to claim 1, wherein the pharmacologically acceptable cyclodextrin is HPβCD.

3. A pharmaceutical composition according to claim 1, wherein the cyclodextrin improves the local tolerance of 4-(4-(2-pyrrolylcarbonyl)-1-piperazinyl)-3-trifluoromethyl-benzoylguanidine or one of the pharmacologically acceptable acid addition salts thereof.

4. A pharmaceutical composition according to claim 1, in a form suitable for intravenous administration.

5. A pharmaceutical composition according to claim 4, wherein the 4-(4-(2-pyrrolylcarbonyl)-1-piperazinyl)-3-trifluoromethyl-benzoylguanidine, or one of the pharmacologically acceptable acid addition salts thereof, is present in a concentration of between 0.6 mg/ml and 40 mg/ml.

6. A method for treating acute myocardial infarction in a patient, comprising administering to said patient a therapeutically effective amount of a pharmaceutical composition according to claim 1.

7. A method for treating of perioperative myocardial necrosis in a patient undergoing a coronary artery bypass operation, comprising administering to said patient a pharmaceutical composition according to claim 1.

8. A pharmaceutical composition comprising a mixture or a complex, or both, of 4-(4-(2-pyrrolylcarbonyl)-1-piperazinyl)-3-trifluoromethyl-beuzoylguanidine, or one of the pharmacologically acceptable acid addition salts thereof, a pharmacologically acceptable cyclodextrin and a hydroxy acid.

9. A pharmaceutical composition according to claim 8, wherein the pharmacologically acceptable cyclodextrin is HPβCD.

10. A pharmaceutical composition according to claim 9, wherein the hydroxy acid is malic acid, acetic acid, lactic acid, tartaric acid or citric acid.

11. A pharmaceutical composition according to claim 10, where the hydroxy acid is citric acid.

12. A pharmaceutical composition according to claim 8, wherein the cyclodextrin and hydroxy acid improve the local tolerance of 4-(4-(2-pyrrolylcarbonyl)-1-piperazinyl)-3-trifluoromethyl-benzoylguanidine or one of thepharmacologically acceptable acid addition salts thereof.

13. A pharmaceutical composition according to claim 8, in a form suitable for intravenous administration.

14. A pharmaceutical composition according to claim 13, wherein the 4-(4-(2-pyrrolylcarbonyl)-1-piperazinyl)-3-trifluoromethyl-benzoylguanidine, or one of the pharmacologically acceptable acid addition salts thereof, is present in a concentration of between 0.6 mg/ml and 40 mg/ml.

15. A method for treating acute myocardial infarction in a patient, comprising administering to said patient a therapically effective amount of a pharmaceutical composition according to claim 8.

16. A method for treating of perioperative myocardial necrosis in a patient undergoing a coronary artery bypass operation, comprising administering to said patient a pharmaceutical composition according to claim 8.

* * * * *